United States Patent [19]

Hodge

[11] Patent Number: 4,827,929
[45] Date of Patent: May 9, 1989

[54] ANGULATED SURGICAL INSTRUMENT

[76] Inventor: Joseph Hodge, 1065 Partridge Rd., Spartanburg, S.C. 29302

[21] Appl. No.: 527,098

[22] Filed: Aug. 29, 1983

[51] Int. Cl.⁴ .................... A61B 17/06; A61B 17/28
[52] U.S. Cl. .................................. 128/321; 128/322; 128/325; 128/340
[58] Field of Search ............... 128/318, 322, 321, 340, 128/325

[56] References Cited

U.S. PATENT DOCUMENTS

| 2,136,414 | 11/1938 | Clements | 128/318 |
| 2,842,132 | 7/1958 | Soltero et al. | 128/322 |
| 3,446,211 | 5/1969 | Markham | 128/322 |
| 3,866,610 | 2/1975 | Kletschka | 128/322 |

FOREIGN PATENT DOCUMENTS 438414  1/1975  U.S.S.R. .............................. 128/346

OTHER PUBLICATIONS

Amico, "Fine Surgical Instruments", Catalog (1966), A.U. 336, p. 114.
Sklar, "Suction and Pressure Apparatus", Catalog (1973), A.U. 336, p. 112.
Mueller, "The Surgical Armamentarium" (1980), A.U. 336, p. 411.
Trylon, "Surgical Instruments", Catalog (1971), p. 644, A.U. 336.

Primary Examiner—Michael H. Thaler
Attorney, Agent, or Firm—Dority & Manning

[57] ABSTRACT

Improved surgical instruments which are angulated to facilitate improved clamping of vessels and suturing when used as a needle holder. Instrument arms are presented which are interrelated along their lengths to define a scissors type motion. The arms include proximal sections having holding and releasable locking capability, intermediate sections at an angle of preferably 80 to 100 degrees with respect to the proximal section, and distal jaw sections that are preferably generally parallel to the proximal sections. Instruments according to the present invention fulfill all the normal physiological and anatomical relationships of function of the hand at the wrist joint which affords improvement over present operative techniques.

12 Claims, 3 Drawing Sheets

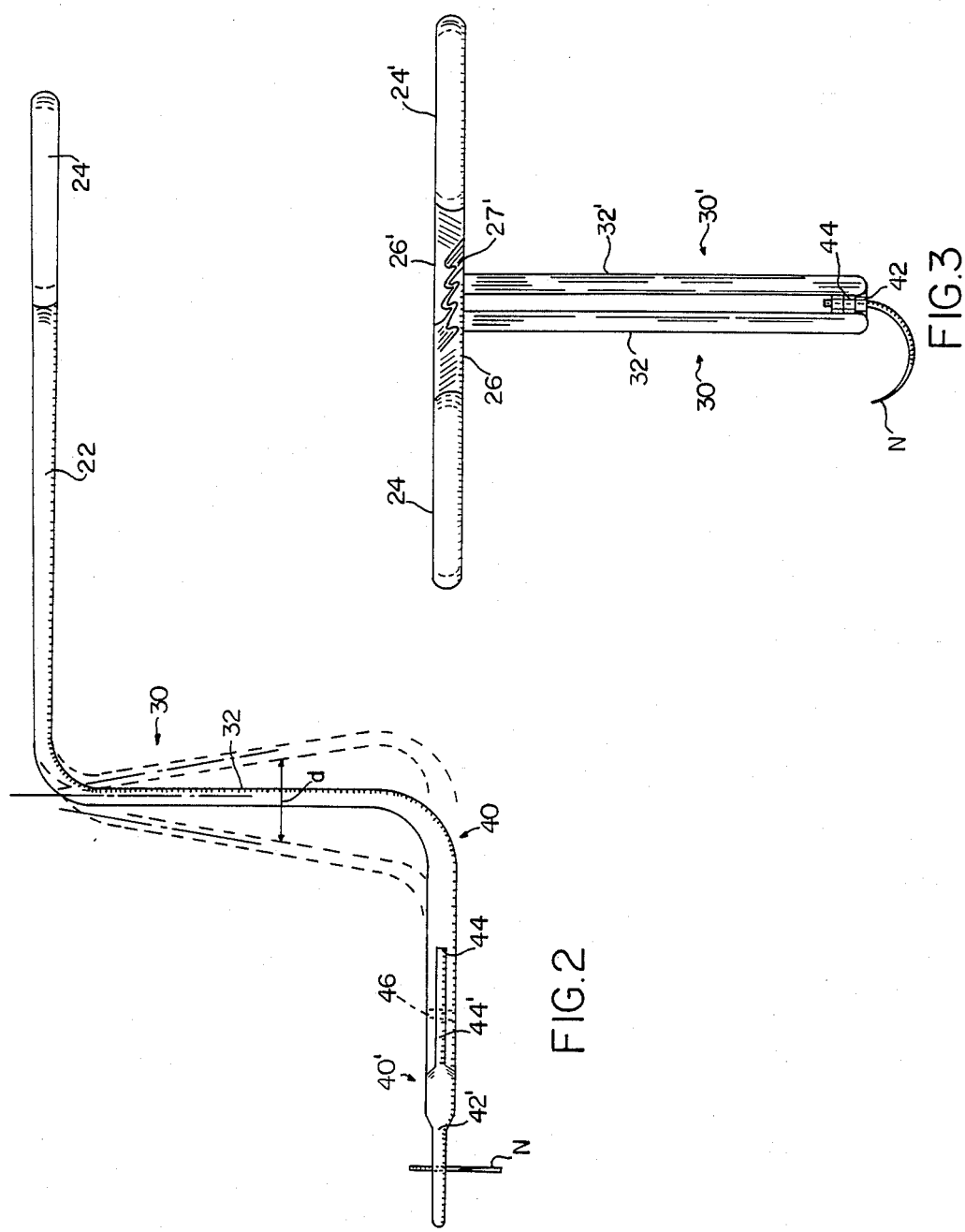

ANGULATED SURGICAL INSTRUMENT

BACKGROUND OF THE INVENTION

The present invention relates to surgical instruments that are angulated to improve utilization and efficiency of use during surgical procedures, primarily internal procedures.

Heretofore, surgical clamps and needle holders have taken the shape of straight, elongated scissors type instruments which include two arms that are pivotally associated at a lock box with the arms lying in a single common plane. For certain such instruments a slight curvature has been presented at the distal tip of same. While the use of such prior art instruments has been great, surgeons using same have experienced limits in occlusion of blood vessels and the like with the clamps, particularly in areas deep, remote and obscure from the surface of the surgical wound. In similar fashion, surgeons utilizing the needle holders or needle clamps have experienced difficulty in suturing within the surgical wound due to the planar elongated nature of the prior art holders, even those which possess a slight curvature of the jaws at the distal end of the instrument.

One particular disadvantage noted with respect to the prior art, conventional instruments is obstruction of the work field. The planar instruments must by nature extend angularly inwardly with respect to the wound and generally across same at the surface, whereby a significant visual blockage of the wound is present, notably that point exactly where the suture is to be produced or the clamp applied.

The surgical instruments of the present invention overcome the disadvantages noted with respect to conventional instruments. Particularly, utilization of the angulated needle holders of the present invention permits easy rectrograde suturing in the placing of posterior row sutures in anastomosing blood vessels, bowel, ureter, and the like. Additionally, when suturing toward oneself, pronation, supination, flexion, extension, adduction, and abduction with actual cicumduction are easily accomplished, such as when suturing the posterior wall of an aortic graft to the aorta. The full range of motion in circumduction is not permitted with a nonangulated needle holder, though with angulated instruments of the present invention, both antegrade and rectrograde suturing can be performed without compromising or restricting circumduction movements which are necessary in the performance of the operative procedures.

By way of explanation as to suturing, the chief joint involved is the wrist joint, with the elbow joint, carpometarcarpal joint, metacarpophalangel joint and shoulder joints contributing synergistically thereto, thus permitting movements necessary in performance of operative procedures.

The wrist joint consists of a radio-carpal, carpal, midcarpal, metacarpal, and distal radial ulnar joint. The radio-carpal joint is disarthroidal, ellipsoidal, in which the concavity formed by the articular surface of the radius and articular disc articulate with the convex surface of the carpal navicular, lunate and triquetral bones, thus allowing flexion, extension, abduction (radial deviation), and adduction (ulnar deviation), thereby permitting circumduction of the hand at the wrist joint.

The capsule of the radiocarpal joint extends from the lower part of the radius and ulna and attaches to the volar surfaces of the navicular, lunate, and triquetral bones. Two ligaments contribute to the stability of the wrist joint, namely the radiocarpal collateral ligament and the ulnar carpal collateral ligament. The radiocarpal extends between the radial styloid and the navicular, while the ulnar collateral attaches between the styloid of the ulna and the triquetral and pisiform bones. The distal radial ulnar joint of the wrist and the proximal radial ulnar of the elbow permit pronation and supination by way of the pronator teres and pronator quadratus muscles along with the supinator and the biceps muscles.

The radio-ulnar joints permit actual rotation, that is pronation and supination, while muscles on the radiocarpal permit flexion, extension, abduction, and adduction.

Movements of the wrist in exerting flexion and extension is through the transverse axis, and radio-carpal deviation is through an anterior-posterior axis. A combination of these movements with pronation and supination allows circumduction of the hand. The range of motion at the metacarpophalangeal joint in flexion is 60 degrees and about 70 degrees in extension, while radial deviation (abduction) is about 20°, and ulnar deviation (adduction) is about 30°. Pronation and supination from the neutral position is about 80° and occur chiefly at the proximal and distal radioulnar joints. Flexion and extension, especially volar flexion, is accentuated by the gliding movement between the proximal and distal rows of the radiocarpal bones at the midcarpal joint of the hand and affords elasticity thereto.

Factors limiting abduction (radial deviation) of the hand at the wrist joint is the styloid process of the radius and the ulnar collateral ligament. Ulnar deviation is more extensive because the radial collateral ligament is weaker than the ulnar collateral ligament, and the styloid process of the ulnar is shorter. In radial deviation, the stronger ulnar collateral ligament and the longer styloid process of the radius restrict abduction due to the greater multangular abutting against the radial styloid.

Operative techniques in suturing or the like are chiefly performed by virtue of articulation at the radiocarpal and proximal distal ulnar carpal joints with synergistic assistance from other joints of the upper extremity as mentioned above. When utilizing instruments of the present invention, the surgical techniques and dexterity are improved leading to more efficient surgical performance as opposed to use of the straight, prior art instruments which do not allow the same degree of freedom of movement. Particularly, from a functional viewpoint, when utilizing a straight needle holder, the hand does not assume the normal position of function, particularly in retrograde suturing, i.e., suturing away from oneself, while conversely a proper attitude is available with instruments of the present invention.

In similar fashion with respect to an angulated surgical instrument of the present invention when the surgeon grasps the clamp between the thumb and volar surfaces of the phalanges, vascular clamps or hemistats according to the present invention extend downwardly into the surgical wound with the distal section of some extending transverse to a vertical axis extending into the wound, whereby the clamping jaw may be more efficiently utilized by the surgeon. Such, for example, permits tangential partial occlusion of the Vena Cava and the Aorta in cases of trauma, without totally occluding blood flow. In the case of the straight vascular clamps, such utilization is not practical due to planarity and length of the instrument. Likewise, the angulated distal tip or jaws of the surgical instrument according to the present invention due to the angulated sections enables the surgeon to more effectively utilize same in virtually all surgical procedures in which a vascular clamp or the like would be utilized.

There is no known prior that is believed to anticipate or suggest the angulated surgical instruments of the present invention.

SUMMARY OF THE INVENTION

It is an object of the present invention to provide an improved surgical instrument for use as a surgical clamp, needle holder, or the like.

A further object of the present invention is to provide an improved surgical instrument that is angulated and defines releaseably lockable jaws at a distal end of same.

Still another object of the present invention is to provide an improved surgical instrument that will facilitate suturing within a surgical wound.

Still further, another object of the present invention is to provide an improved surgical instrument that does not obstruct the field of view of the surgeon using same.

Yet another object of the present invention is to provide an improved needle holder for use in surgical techniques, such that a surgeon using same may easily accomplish pronation, supination, flexion, extension, adduction, and abduction, with actual circumduction of the instrument while maintaining a virtually unobstructed view of the field in which the surgeon is working.

Generally speaking, the improved surgical instrument according to teachings of the present invention comprises a pair of arms, said arms being interrelated intermediate their lengths and defining a pivot point thereat, said arms having a first, or proximal generally straight section, said first straight sections having holding means located at outer free ends of same, said first straight sections further having releaseable locking means associated therewith, said arms having second, intermediate sections extending at a predetermined angle from said first sections, and said arms having third, distal sections extending from said second, intermediate sections at an angular relationship, such said distal sections reside in planes generally parallel to said first arm sections, said distal sections cooperating to define clamping jaws along at least a portion of the length of the same, whereby said second and third sections of said instrument may be more efficiently employed within surgical wound for clamping and suturing by the surgeon.

More specifically, the improved surgical instrument according to teachings of the present invention is angulated, such that the two arms defining same in pivotal arrangement with a scissors type connection extend in a first, proximal section along a horizontal plane, then bend downwardly at an angle of approximately 80 to 100 degrees, preferably about 90 degrees, defining an elongated section for placement of the instrument within the surgical wound, and a third, distal section that extends outwardly from said second section at an angle from about 80° to about 100° with respect thereto, preferably about 90 degrees, said third sections defining clamping jaws therebetween for utilization as a hemistat, vascular clamp or the like or for securely holding a suture needle therebetween. Releaseable locking means are provided along with holding means at outer free end of the first arm sections, such that the surgeon may manipulate the instrument with one hand to releaseably lock the jaws in a clamping position, or with the jaws securely holding a suture needle, to permit the surgeon to more easily manipulate the instrument for internal suturing within the wound.

In a most preferred arrangement, the interrelationship between the arms of the surgical instrument is provided by one arm passing through an opening defined in the other of said arms, with a pivot pin securely interrelating the two arms. The releaseable locking means are preferably oppositely located serrations or elements that are secured to the first arm sections and extend outwardly therefrom in the direction of the other serrations, such that when the serrations are brought into engagement, shoulders of one set of serrations engage shoulders of the opposite set of serrations to lock the arms at the desired location. Vertical displacement of the arms will disengage the shoulders. In an embodiment in which the instrument according to the present invention is utilized as a needle holder, hardened metal jaw surfaces or elements are secured along inside surfaces of the distal ends of the arms to define clamping surfaces. Preferably hardened metal elements are provided by Tungsten carbide plates that are appropriately secured by any acceptable means to the inside surfaces of the arms.

BRIEF DESCRIPTION OF THE DRAWINGS

FIG. 2 is a side elevational view of the surgical instrument as depicted in FIG. 1, illustrated with a suture needle secured therewithin.

FIG. 3 is a rear elevational view of the surgical instrument as shown in FIG. 1, likewise depicting a suture needle being held thereby.

DESCRIPTION OF THE PREFERRED EMBODIMENTS

Figure 1:
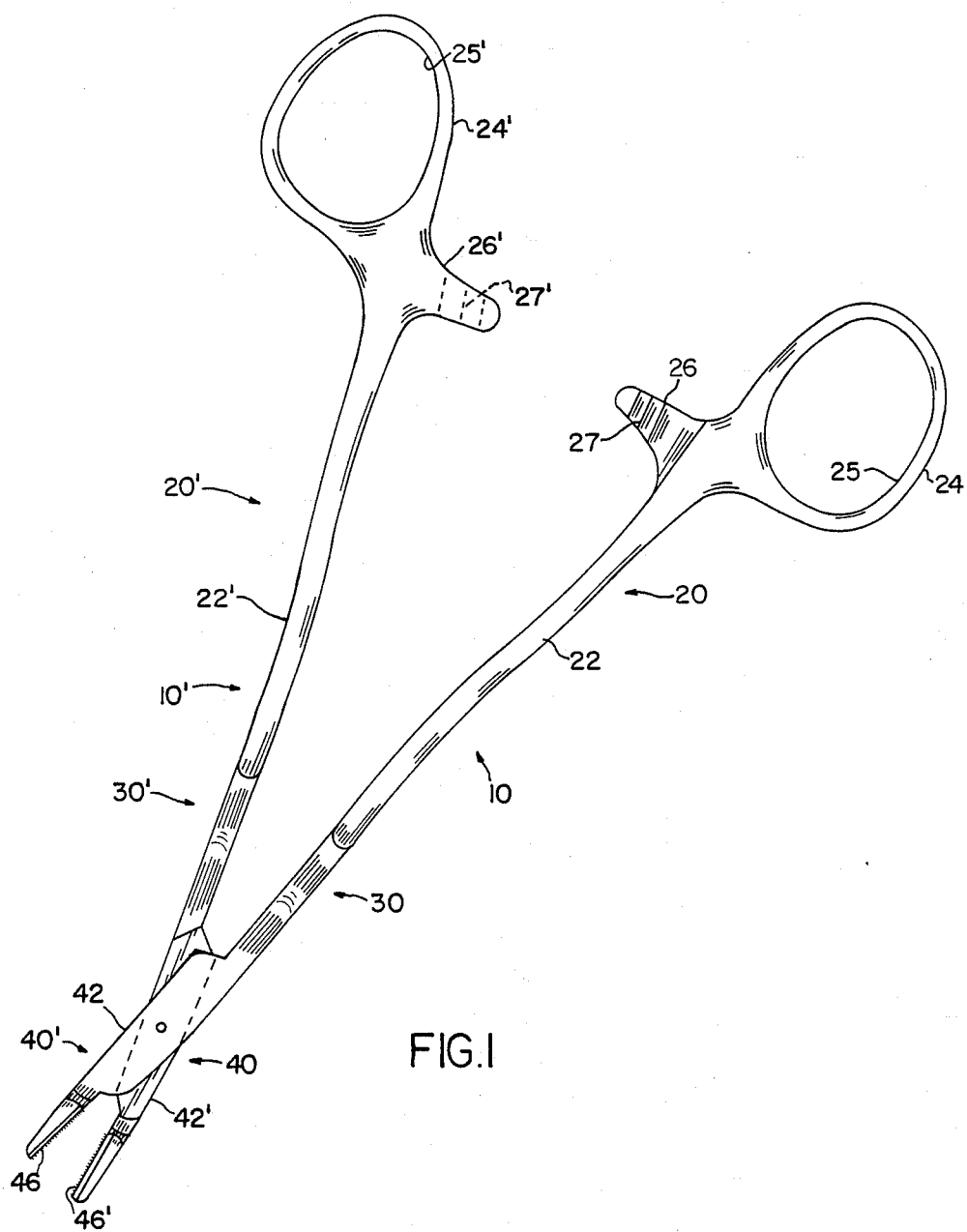
FIG. 1 is a top planar view of a surgical instrument according to teachings of the present invention.

Making reference to the Figures, preferred embodiments of the present invention will now be described in detail. A surgical instrument according to teachings of the present invention taking the form of a needle holder is illustrated in FIGS. 1-3. The needle holder includes a pair of arms 10, 10' generally, with each arm being divided into a first or proximal generally planar section 20, 20', an intermediate angulated section generally 30, 30' and a distal or jaw section generally 40, 40'. Planar sections 20, 20' include an elongated portion 22, 22' having a holding means 24, 24' at a rear outer free end of same. Preferably as illustrated in FIG. 1, holding means 24, 24' include finger or thumb receiving openings 25, 25', such that a surgeon may insert a thumb and one finger into opposite openings 25, 25' and thus manipulate the needle holder. Arms 10, 10' are interrelated along their lengths to define a pivot point, such that manipulation of arms 10, 10' will open and close the arm jaw sections 40, 40', such that a suture needle N may be securely held therein. Locking means 26, 26' upon engagement will thus releasably lock the needle between jaw sections 40, 40'.

Making particular reference to FIGS. 2 and 3, it can be seen that angulated arm sections 32, 32' extend from straight arm sections 22, 22' at a most preferred angle of approximately 90 degrees with respect thereto. As shown in phantom, however, angulated sections 32, 32' are preferably presented at an angle in a range of about 80 to about 100 degrees with respect to arm sections 22, 22', though other angles could likewise be utilized, though with a lesser degree of effectiveness. Further, at a lower end of angulated arm sections 32, 32', the terminal ends 40, 40' take a further most preferred approximately 90 degree turn, and as seen in FIG. 2, terminal arm sections 40, 40' are thus preferably generally parallel to first straight sections 22, 22'. Again, however, an angular bend between angulated arm sections 30, 30' and terminal arm sections 40, 40', preferably reside in a range of about 80 to about 100 degrees. Terminal arm sections 40, 40' extend from angulated section 30 and are provided with jaw sections 42, 42'. Terminal arm section 40 defines an opening 44 therewithin through which a portion of terminal arm section 40' extends to provide a scissors type arrangement and with a pivot pin 46 passing therethrough to secure the relationship between arms 10, 10', such that a pivot point is located about pin 46, around which jaws 42, 42' may pivot between an open or closed position.

With a suture needle N held between jaws 42, 42' as shown in FIGS. 2 and 3, latching or locking means 26, 26' are brought into engagement, such that serrations or shoulders 27, 27' mate to preclude against separation of arm sections 22, 22' about pivot point 46. Suture needle N is thus securely locked in place. With such an arrangement, the surgeon may then simply lower the distal sections 40, 40' and the angulated sections 30, 30' into the surgical wound, where the particular body portion may be sutured as needed. With the angulated arrangement as depicted in FIGS. 1–3, as mentioned hereinbefore, first the surgeon's field of view of the wound is not obstructed nearly so much as when a straight surgical instrument is being utilized. Moreover, based on the anatomical presentation set forth above, utilizing a needle holder of the present invention as exemplified in FIGS. 1–3, the surgeon has a full range of motion or circumduction about the wrist which greatly facilitates the suturing procedure above and beyond that conventionally accomplished, not to mention that the surgeon will not become fatigued as quickly.

Figure 4:
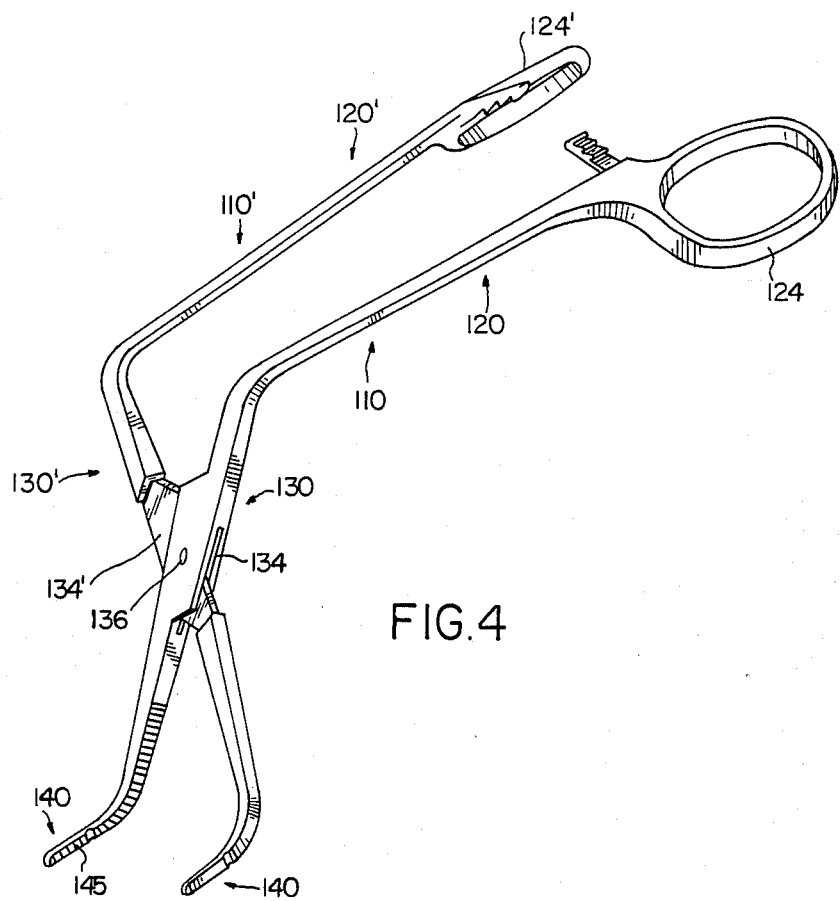
FIG. 4 is an isometric view of a further embodiment of the surgical instrument according to teachings of the present invention.

A further embodiment of the present invention is shown in FIG. 4 and includes a pair of arms 110, 110' which have a first flat, proximal arm section 120, 120' generally, an angulated intermediate section 130, 130' generally, and a terminal or distal, jaw section 140, 140' generally. Since the structure of the surgical instrument depicted in FIG. 4 is very similar to that depicted in FIGS. 1–3, only the general differences in same will be discussed. Note, for example, that intermediate angulated section 130 defines an opening 134 therein, while a portion 134' of arm section 130' is received therethrough, and interconnected by way of a pivot pin 136. In the embodiment of FIGS. 1–3, the pivotal relationship occurred in the terminal jaw sections 40, 40', whereas in this particular embodiment, the pivot point 136 is located along the angulated intermediate sections 130, 130'. Furthermore, the embodiment illustrated in FIG. 4 which is intended to be a hemistat or clamp, utilizes a shorter terminal jaw section 140, 140' than with the needle holders shown in FIGS. 1–3. In this vein, jaw sections 140, 140' are provided with serrations 145, 145' along the inner opposite surfaces of same to facilitate appropriate contact between the instrument and the body part to be clamped. Serrations 145, 145' extend upwardly along a portion of intermediate angular arm sections 130, 130' in a preferred embodiment. Hence, should a surgeon desire to utilize an instrument according to the present invention intended to be utilized as a clamp, the vessel or other body part to be clamped would be received between serrations 145, 145' of jaws 140, 140' and arms 110, 110' would be brought together at the holding means 124, 124' locking same in position to securely, releaseably set the jaws in the clamping position.

Preferably, instruments according to teachings of the present invention are produced from high technology metals, such as stainless steels, whereby resterilization of same may be achieved conveniently and effectively. Likewise though, the pivot point is shown as a lock box, obviously the two arms could be interrelated such that one simply lies across the top of the other, with the pivot pin extending therethrough.

In the chest, pelvis and other deep and small surgical wounds that do not readily admit conventional instruments, the angulated instruments according to the present invention permit accurate placement of jaws 40, 40' or 140, 140' directly onto or adjacent the operative target for suturing or clamping. The short jaws of the angulated instruments permit improved visual exposure of the target and allow unrestricted circumduction, both of which enhance dexterity and ease of instrument tying. Operative time is thus shortened and accurately of suturing and clamping is more precise and effective.

Having described the present invention in detail, it is obvious that one skilled in the art will be able to make variations and modifications thereto without departing from the scope of the invention. Accordingly, the scope of the present invention should be determined only by the claims appended hereto.

That which is claimed is:

1. An improved surgical instrument comprising a pair of arms, said arms being interrelated intermediate their lengths and defining a pivot point thereat, each of said arms having a first generally straight section, said first straight sections having holding means located at an outer free end of same, said first straight sections further having releasable locking means associated therewith; each of said arms having a second, intermediate section extending downwardly from said first section at an angle of from about 80 to about 100 degrees with respect thereto; and said arms having third terminal sections extending from said second, intermediate sections in a plane generally parallel to said first arm sections and generally in an axial direction with respect thereto, said third terminal sections cooperating to define clamping jaws along at least a portion of the length of same, whereby said second and third sections of said instrument may be more easily employed within surgical wounds for clamping and suturing by the surgeon.

2. The instrument as defined in claim 1 wherein said holding means comprise finger receiving areas defined by said arms.

3. The instrument as defined in claim 1 wherein said releaseable locking means comprise opposing serrations secured to each arm and extending inwardly therefrom in the direction of the opposite arm.

4. The instrument as defined in claim 1 wherein one of said arms defines an opening in one of said sections and the other arm passes therethrough, said arms being pivotally secured thereat.

5. The instrument as defined in claim 1 wherein said third section of said arms is presented at an angle with respect to said second section of from about 80 to about 100 degrees.

6. The instrument as defined in claim 1 wherein said arms define gripping surfaces along opposite inside surfaces of same.

7. The instrument as defined in claim 6 wherein said gripping surfaces are serrated.

8. The instrument as defined in claim 1 wherein said gripping surfaces are defined by hardened metal members secured to an inside surface of said arms.

9. An improved surgical instrument comprising a pair of arms, said arms being interrelated along their lengths and defining a pivot point thereat to permit a scissors type action thereabout, each of said arms having a first generally straight section, each of said first sections having holding means at an outer free end of same, said first sections further have releasable locking means adjacent said holding means; each of said arms further having a second section, said second section extending downwardly from said first sections at an angle in a range of from about 80 to about 100 degrees with respect to said first section, said arms further including a third section, said third sections being generally parallel with said first sections extending in a general axial direction with respect to said first sections, and defining clamping jaws, said pivot point being located along one of said second and third sections; whereby during surgery said second and third arm sections may be received within a surgical wound for more ready access and articulation with respect to internal body tissues, vessels, and organs.

10. The instrument as defined in claim 9 wherein said releaseable locking means comprise opposing serrations associated with said arms and extending outwardly therefrom in the direction of said opposite serrations.

11. The instrument as defined in claim 9 wherein said clamping jaws are adapted to receive a suture needle therebetween.

12. The instrument as defined in claim 9 wherein said third arm section defines a holding surface along facing inside surfaces of same.

* * * * *